United States Patent
Schwab et al.

(10) Patent No.: US 9,655,757 B2
(45) Date of Patent: May 23, 2017

(54) ENDOLUMENAL ESOPHAGEAL RESTRICTION DEVICE

(71) Applicant: Apollo Endosurgery, Inc., Austin, TX (US)

(72) Inventors: Justin Schwab, Santa Barbara, CA (US); Zachary Dominguez, Santa Barbara, CA (US); Jason Metzner, Covington, WA (US)

(73) Assignee: Apollo Endosurgery US, Inc., Austin, TX (US)

( * ) Notice: Subject to any disclaimer, the term of this patent is extended or adjusted under 35 U.S.C. 154(b) by 0 days.

(21) Appl. No.: 14/874,584

(22) Filed: Oct. 5, 2015

(65) Prior Publication Data

US 2016/0022460 A1    Jan. 28, 2016

Related U.S. Application Data

(62) Division of application No. 13/356,401, filed on Jan. 23, 2012, now Pat. No. 9,149,383.

(51) Int. Cl.
*A61F 5/00* (2006.01)

(52) U.S. Cl.
CPC ........... *A61F 5/0076* (2013.01); *A61F 5/003* (2013.01); *A61F 5/005* (2013.01); *A61F 5/0079* (2013.01); *A61F 2220/0016* (2013.01); *A61F 2220/0083* (2013.01)

(58) Field of Classification Search
CPC ........ A61F 5/0076; A61F 5/003; A61F 5/005; A61F 5/0079
USPC ........................................................ 604/8–9
See application file for complete search history.

(56) References Cited

U.S. PATENT DOCUMENTS

| | | | |
|---|---|---|---|
| 7,431,725 B2 | 10/2008 | Stack et al. | |
| 7,981,162 B2 | 7/2011 | Stack et al. | |
| 8,029,455 B2 * | 10/2011 | Stack | A61F 5/0076 604/8 |
| 2004/0148034 A1 * | 7/2004 | Kagan | A61F 2/04 623/23.65 |
| 2004/0243152 A1 | 12/2004 | Taylor et al. | |
| 2005/0247320 A1 | 11/2005 | Stack et al. | |
| 2007/0293716 A1 * | 12/2007 | Baker | A61F 2/04 600/37 |
| 2009/0012541 A1 * | 1/2009 | Dahl | A61B 17/0401 606/151 |
| 2009/0018389 A1 | 1/2009 | Laufer et al. | |
| 2009/0247992 A1 | 10/2009 | Shalon et al. | |
| 2010/0137891 A1 | 6/2010 | Shalon et al. | |
| 2011/0092879 A1 | 4/2011 | Baker et al. | |

\* cited by examiner

*Primary Examiner* — Leslie Deak
*Assistant Examiner* — Kai Weng
(74) *Attorney, Agent, or Firm* — Gordon & Jacobson, P.C.

(57) ABSTRACT

Generally described herein are apparatus, systems and methods related to a novel esophageal device implantable in the patient's body and designed to replicate the restrictive and satiety mechanism associated with gastric banding systems known in the art. The device can be a compliant and tubular-shaped and fixated within the gastro-esophageal lumen using tissue anchors.

20 Claims, 13 Drawing Sheets

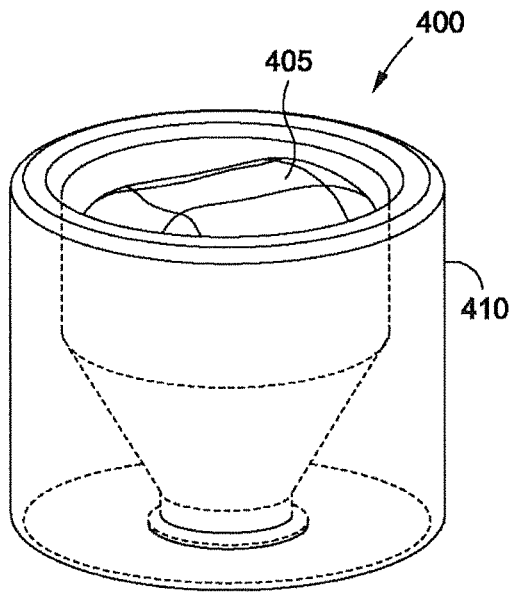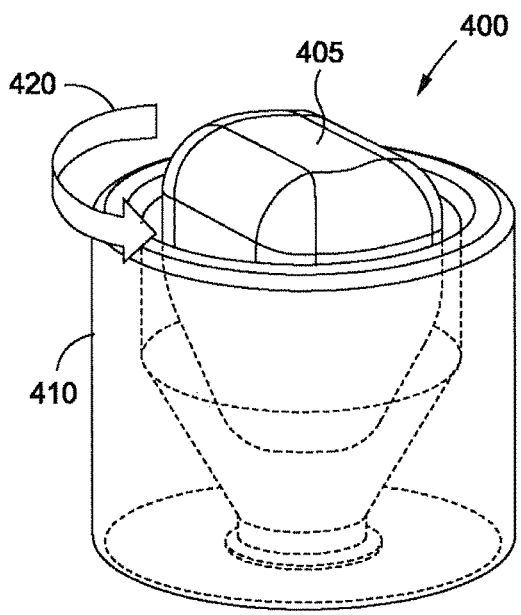
FIG. 4A  FIG. 4B
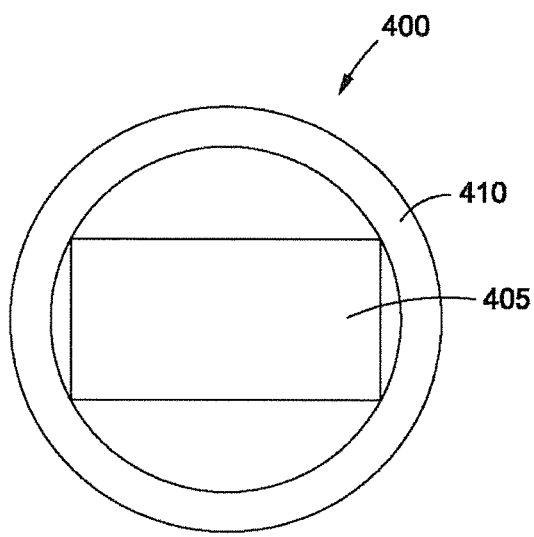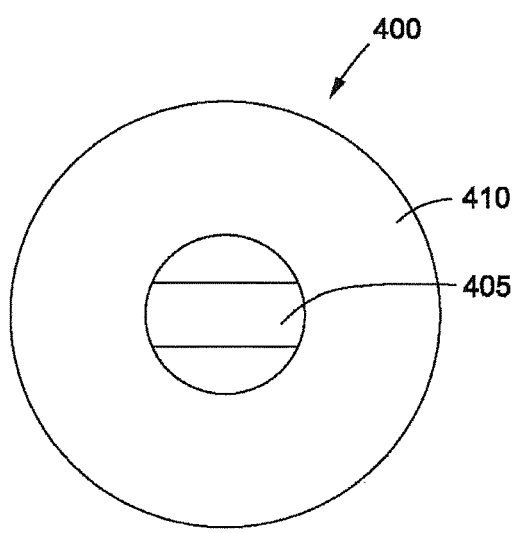
FIG. 4C  FIG. 4D

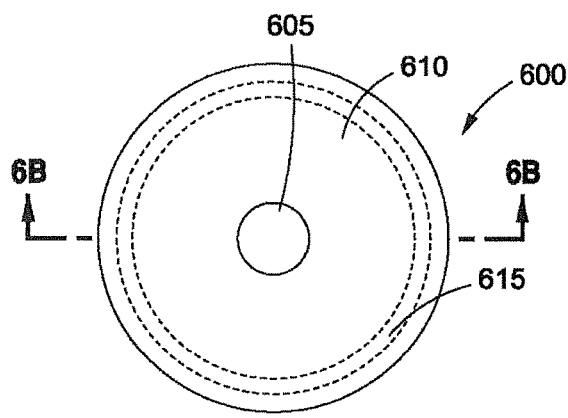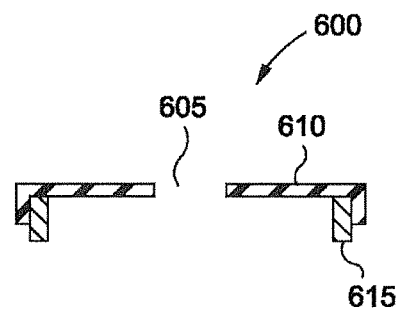
FIG. 6A          FIG. 6B
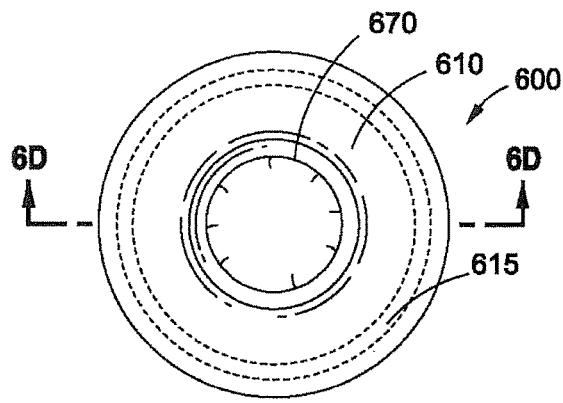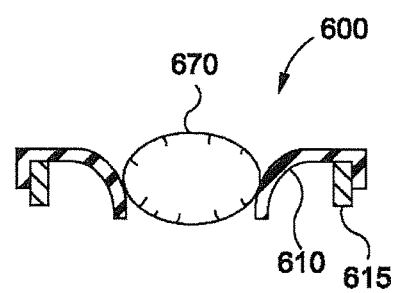
FIG. 6C          FIG. 6D
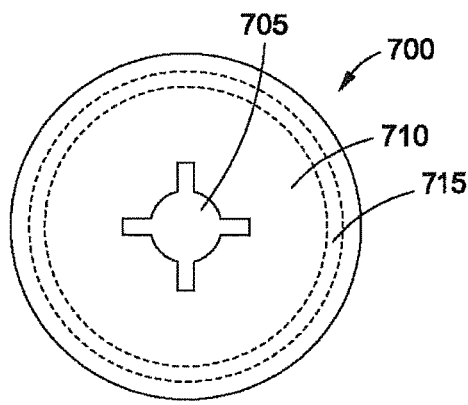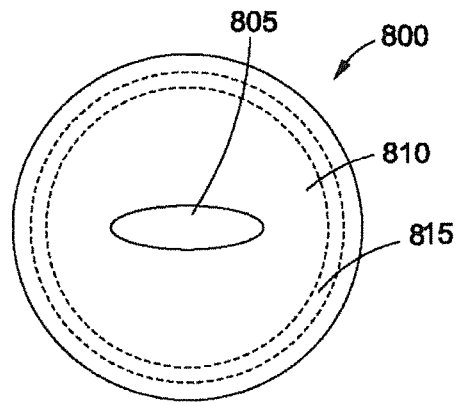
FIG. 7          FIG. 8

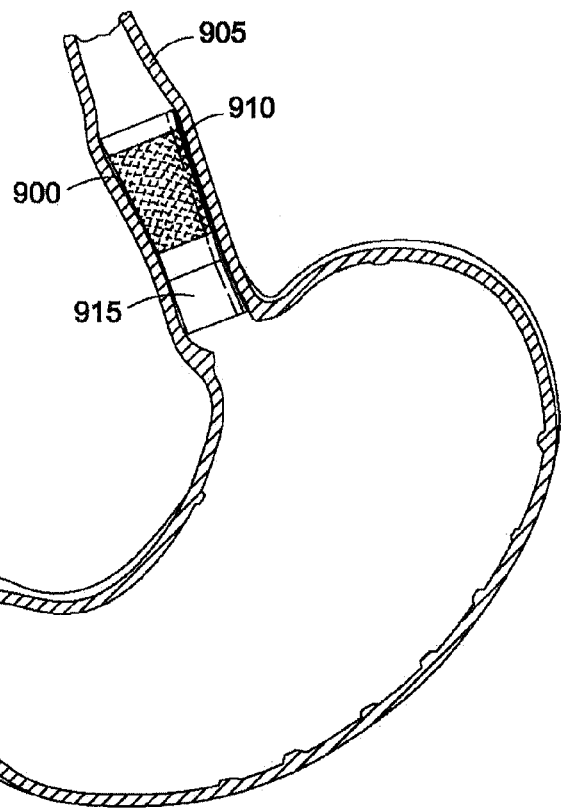
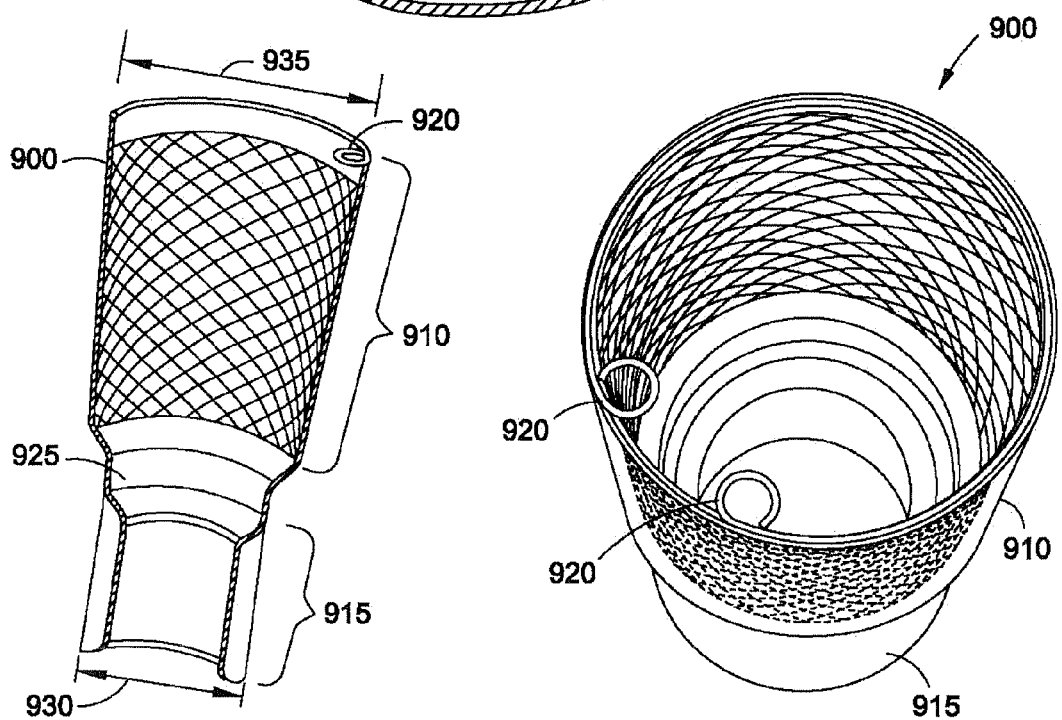
FIG. 9A
FIG. 9B
FIG. 9C

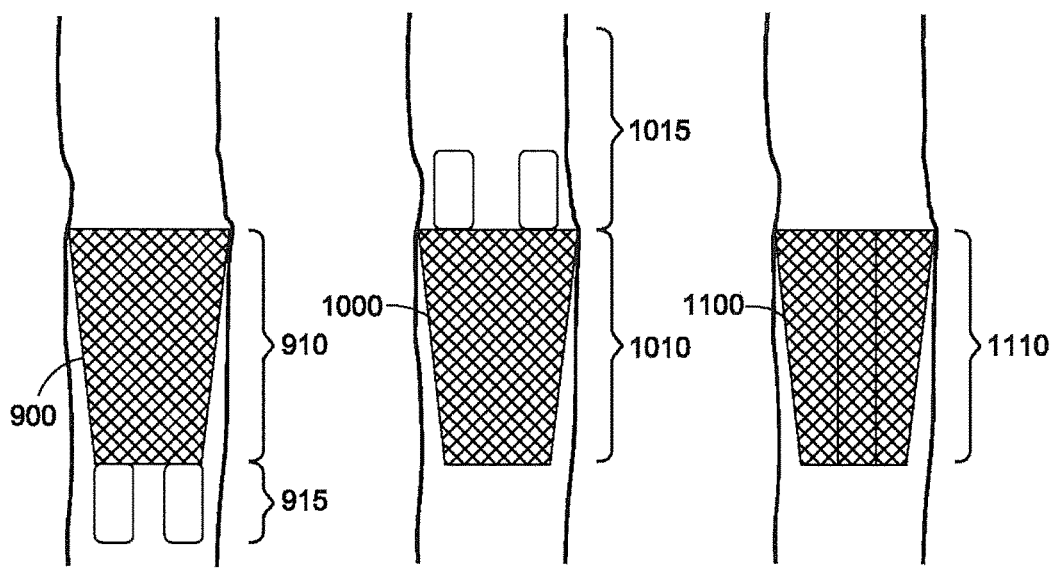
FIG. 9D  FIG. 10  FIG. 11

ENDOLUMENAL ESOPHAGEAL RESTRICTION DEVICE

CROSS-REFERENCE TO RELATED APPLICATION

This application is a divisional of application Ser. No. 13/356,401, filed on Jan. 23, 2012, the entire contents of which are incorporated herein by reference.

FIELD

The present invention generally relates to medical systems, devices and uses thereof for treating obesity and/or obesity-related diseases. More specifically, the present invention relates to an implant for replicating one or more satiety inducing mechanisms associated with gastric banding system.

BACKGROUND

Gastric banding apparatus have provided an effective and substantially less invasive alternative to gastric bypass surgery and other conventional surgical weight loss procedures. Despite the positive outcomes of invasive weight loss procedures, such as gastric bypass surgery, it has been recognized that sustained weight loss can be achieved through a laparoscopically placed gastric band (e.g., the LAP-BAND® (Allergan, Inc., Irvine, Calif.) gastric band or the LAP BAND AP® (Allergan, Inc., Irvine, Calif.) gastric band). Generally, gastric bands are placed about the cardia, or upper portion, of a patient's stomach forming a stoma that restricts the food's passage into a lower portion of the stomach. When the stoma is of an appropriate size that is restricted by a gastric band, food held in the upper portion of the stomach may provide a feeling of satiety or fullness that discourages overeating.

The interface between the physician and the patient at any point post-operation is generally limited to the physician injecting or removing fluid via the access port implanted in the patient's body to further promote weight loss. Metrics such as volume, pressure and patient response (e.g., vomiting, nausea, poor weight loss, and the like) are monitored to determine appropriate band pressure and stoma size.

However, certain patients might not desire having an access port implanted, for instance, as the access port may be aesthetically unpleasing. Therefore, what is needed is an alternative obesity treatment system.

Some attempts have been made to provide for an alternative obesity treatment system. For example, Kagan, et al., U.S. Patent Pub. No. 2004/0148034, discloses a non-adjustable artificial stoma implant with a connection to a gastric sleeve as illustrated in FIG. 1A. However, the cuff and sleeve of Kagan, et al., is very complex and may require an invasive implantation/removal procedure. In addition, the cuff and sleeve of Kagan do not replicate an internal gastric band. More particularly, the cuff functions as an anchor for the malabsorptive gastric sleeve and does not assist the peristaltic bolus transport.

Laufer, et al., U.S. Patent Pub. No. 2009/0018389, discloses performing restriction via tissue plication with adjustability from technique as illustrated in FIG. 1B. However, performing restriction via tissue plication has been shown to encourage erosion and/or necrosis.

Stack, et al., U.S. Pat. No. 7,431,725, discloses forming plications and then coupling or seating medical devices against the plications as illustrated in FIG. 1C. However, such a system also suffers from the drawback of encouraging erosion and/or necrosis.

Shalon, et al., U.S. Patent Pub. No. 2010/0137891, discloses a passive GEJ implant for treatment of GERD as illustrated in FIG. 1D. However, the system of Shalon, et al., does not function to limit food transport into the stomach, but only discourages reflux from entering the esophagus to combat excessive GERD.

Taylor, et al., U.S. Patent Pub. No. 2004/0243152, discloses stomach volume restriction via serosal constriction as illustrated in FIG. 1E. However, Taylor, et al., requires a very complex system which includes rotating inner and outer device layers.

However, neither of these provide for a self-adjusting esophageal dilation implant for the treatment of obesity, or related apparatus, methods or systems thereof.

SUMMARY

Generally described herein are apparatus, systems and methods related to a novel esophageal device implantable in the patient's body and designed to replicate the restrictive and satiety mechanism associated with gastric banding systems known in the art. In one or more embodiments, the device can be a compliant and tubular-shaped artificial stoma and fixated within the gastro-esophageal lumen using tissue anchors.

In this manner, the device is a minimally invasive, non-surgical alternative to existing restriction and satiety inducing devices currently used to treat obesity. In addition, the device is compliant and may, in certain embodiments, require no direct adjustment performed by a physician. The highly compliant nature of the device renders it self-adjusting (and thus obstruction tolerant) such that the device can form and shape with peristalsis, thereby naturally moving the bolus through the restriction. Even in the embodiments which allows for physician adjustments, implant manipulation is performed under full endoscopic vision. Furthermore, the device can be removed non-surgically, using full endoscopic instrumentation. This provides a benefit to patients who are adverse to surgery or cannot be operated on.

An intragastric device for the treatment of obesity is described and shown. The intragastric device includes a compliant portion containing a gel, an anchoring portion defining an opening and integral with the compliant portion, and a tissue fixation component for insertion through the opening of the anchoring portion. The tissue fixation component is capable of penetrating or configured to penetrate a patient tissue to attach the anchoring portion and the compliant portion in an intragastric position, thereby treating obesity. The opening can be a hole, a lumen, a channel, an orifice, or other space that can receive or allow passage of the tissue fixation component.

In one embodiment, provided is an endoscopic device fixable to a patient's mucosal-serosal tissue for the treatment of obesity. The endoscopic device includes a compliant portion filled with a gel for emulating natural peristaltic behavior, an anchoring portion connected to the compliant portion having a plurality of holes, and a tissue fixation component for penetrating a corresponding hole of the plurality of holes. The tissue fixation component is configured for further penetrating the patient's mucosal-serosal tissue to fix the anchoring portion and the compliant portion in place.

In one embodiment, provided is an endoscopic device fixable to a patient's mucosal-serosal tissue for the treatment of obesity. The endoscopic device includes a compliant, low-durometer body housing a low viscosity fluid and configured to emulate natural peristalsis such that when a bolus of food contacts a top portion of the housing, the fluid is transferred in a downward direction, and when the bolus of food contacts a middle portion of the housing, the fluid is transferred in both an upward and downward direction, and when the bolus of food contacts a bottom portion of the housing, the fluid is transferred in an upward direction.

In one embodiment, provided is an endoscopic device fixable to a patient's mucosal-serosal tissue for the treatment of obesity. The endoscopic device includes a housing defining a food passage, and a conical valve housed within the housing. The conical valve is configured for controlling a restriction of the food passage such that reducing separation between the housing and the conical valve increases the restriction of the food passage.

In one embodiment, provided is an endoscopic device fixable to a patient's mucosal-serosal tissue for the treatment of obesity. The endoscopic device includes a housing defining an opening, and a plurality of pivotable plates attached to the housing such that manipulation of the plates controls a size of the opening.

In one embodiment, provided is an endoscopic device insertable into a patient's digestive track and for the treatment of obesity. The endoscopic device includes a stent for migration resistance and for maintaining fixation to a patient's digestive tract when implanted into the patient's digestive tract, the stent defining a passageway for a bolus of food, a gel-filled, pliable and compliant artificial stoma for emulating natural peristaltic behavior and further extending the passageway for the bolus of food, the artificial stoma coupled to the stent, and a liner disposed between the stent and the artificial stoma, the liner configured to couple the stent to the artificial stoma and further extending the passageway for the bolus of food.

BRIEF DESCRIPTION OF THE DRAWINGS

The features, obstacles, and advantages of the present invention will become more apparent from the detailed description set forth below when taken in conjunction with the drawings, wherein:

FIG. 4A illustrates a conical valve in a first position according to an embodiment of the present invention.

FIG. 4B illustrates the conical valve of FIG. 4A in a second position according to an embodiment of the present invention.

FIG. 4C illustrates a top view of the conical valve of FIG. 4A according to an embodiment of the present invention.

FIG. 4D illustrates a bottom view of the conical valve of FIG. 4A according to an embodiment of the present invention.

FIG. 6A illustrates a top view of an endoscopic device having a variably sized opening according to an embodiment of the present invention.

FIG. 6B illustrates a cross sectional, side view of the endoscopic device of FIG. 6A according to an embodiment of the present invention.

FIG. 6C illustrates a top view of the endoscopic device of FIG. 6A transporting a bolus of food according to an embodiment of the present invention.

FIG. 6D illustrates a cross sectional, side view of the endoscopic device of FIG. 6A transporting a bolus of food according to an embodiment of the present invention.

FIG. 7 illustrates a top view of an endoscopic device having a variably sized opening according to an embodiment of the present invention.

FIG. 8 illustrates a top view of an endoscopic device having a variably sized opening according to an embodiment of the present invention.

FIG. 9A illustrates one embodiment of an endoscopic device disposed within the esophagus of a patient according to an embodiment of the present invention.

FIG. 9B illustrates the endoscopic device of FIG. 9A according to an embodiment of the present invention.

FIG. 9C illustrates a top perspective view of the endoscopic device of FIG. 9A according to an embodiment of the present invention.

FIG. 9D illustrates a side view of the endoscopic device of FIG. 9A according to an embodiment of the present invention.

FIG. 10 illustrates one embodiment of an endoscopic device disposed within the esophagus of a patient according to an embodiment of the present invention.

FIG. 11 illustrates one embodiment of an endoscopic device disposed within the esophagus of a patient according to an embodiment of the present invention.

DETAILED DESCRIPTION

Apparatuses, systems and/or methods that implement the embodiments of the various features of the present invention will now be described with reference to the drawings. The drawings and the associated descriptions are provided to illustrate some embodiments of the present invention and not to limit the scope of the present invention. Throughout the drawings, reference numbers are re-used to indicate correspondence between referenced elements.

Figure 1A:
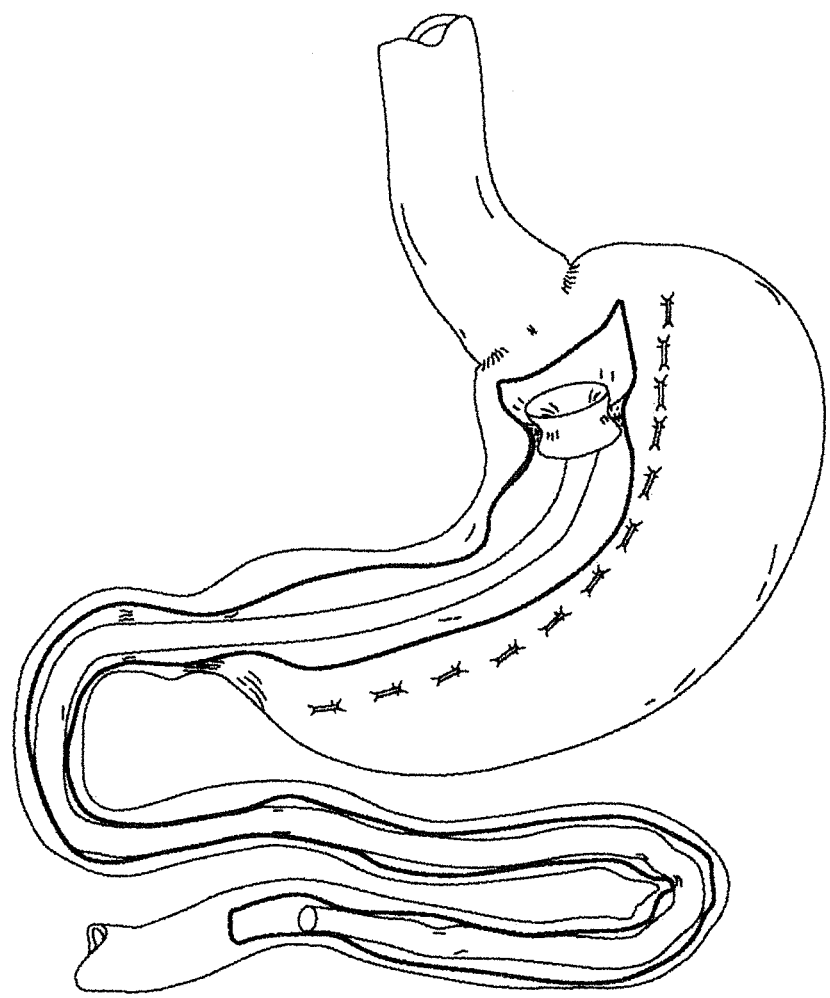
FIG. 1A illustrates a prior art, non-adjustable artificial stoma implant with a connection to a gastric sleeve.
Figure 1B:
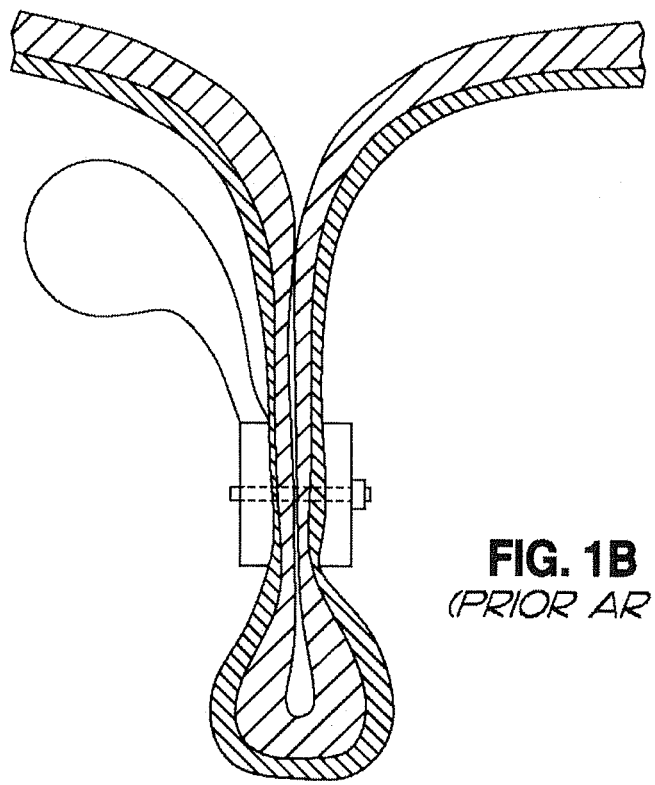
FIG. 1B illustrates a prior art, tissue plication device.
Figure 1C:
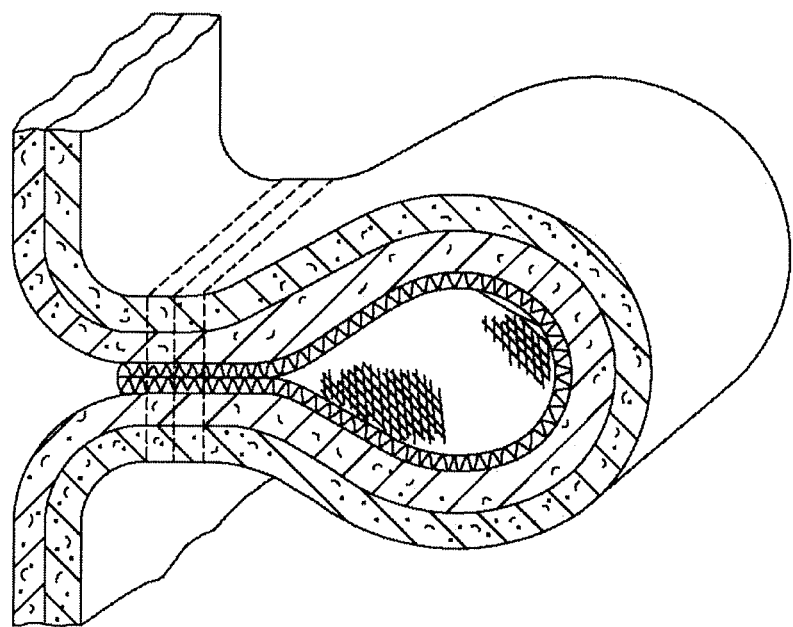
FIG. 1C illustrates a prior art, tissue plication device.
Figure 1D:
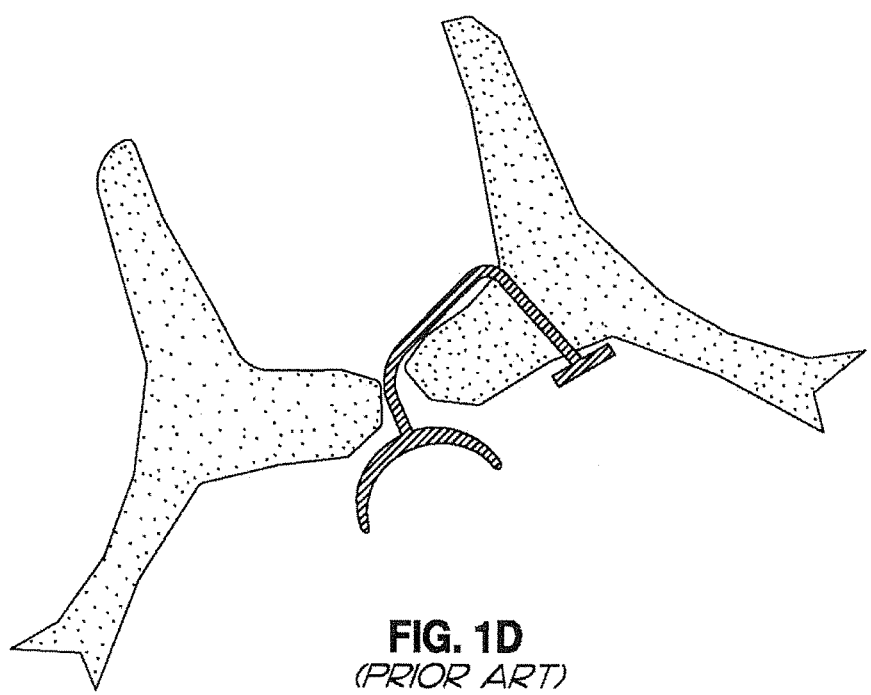
FIG. 1D illustrates a prior art, GEJ implant for treatment of GERD.
Figure 1E:
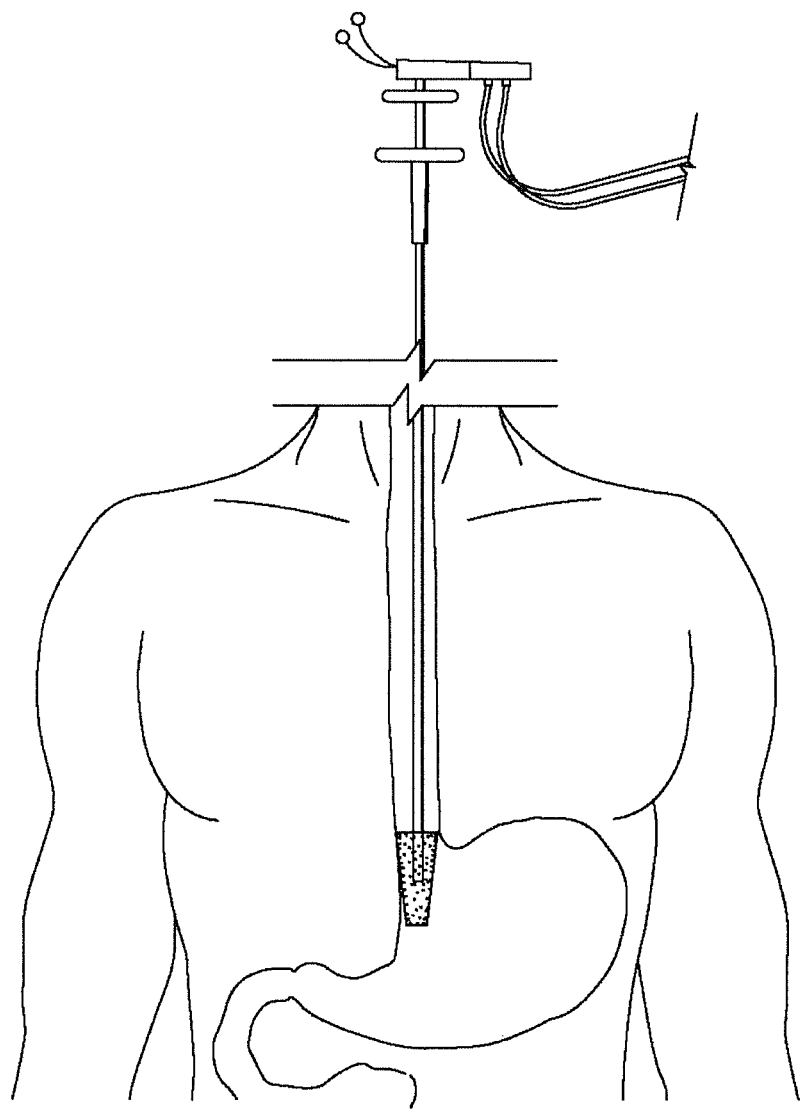
FIG. 1E illustrates a prior art, stomach volume restriction via serosal constriction.
Figure 2A:
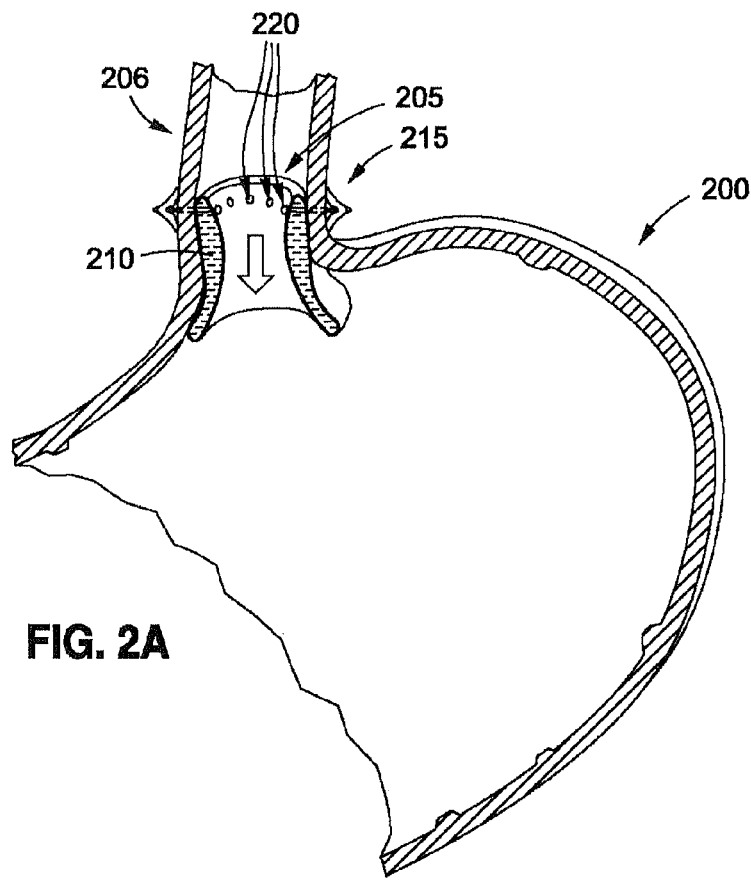
FIG. 2A illustrates a self-adjusting esophageal implant according to an embodiment of the present invention.

FIG. 2A illustrates an esophageal implant device 205 implanted into a patient's esophageal junction between an esophagus 206 and a stomach 200. These devices can also be referred to as intragastric devices. As shown, the esophageal implant device 205 is fixed within the esophageal lumen via tissue fixation means 215 anchoring the esophageal implant device 205 in place through a plurality of holes 220. That is, each of the plurality of holes 220 may have its own corresponding tissue fixation means 215. Furthermore, the number of holes 220 and corresponding tissue fixation means 215 may be configured as desired.

The esophageal implant device 205 functions to emulate natural tissue behavior (e.g., esophageal constriction, expansion, peristalsis, and the like) to allow the transport of food boluses through the esophageal implant device 205, albeit at a potentially slower rate due to the restriction caused by the esophageal implant device 205. More particularly, the natural tissue behavior emulated by the esophageal implant device 205 is produced, at least in part, by the compliance of the esophageal implant device 205 which may be due to the gel (or saline) or other appropriate compliance producing filling 210.

Figures 2B, 2C:
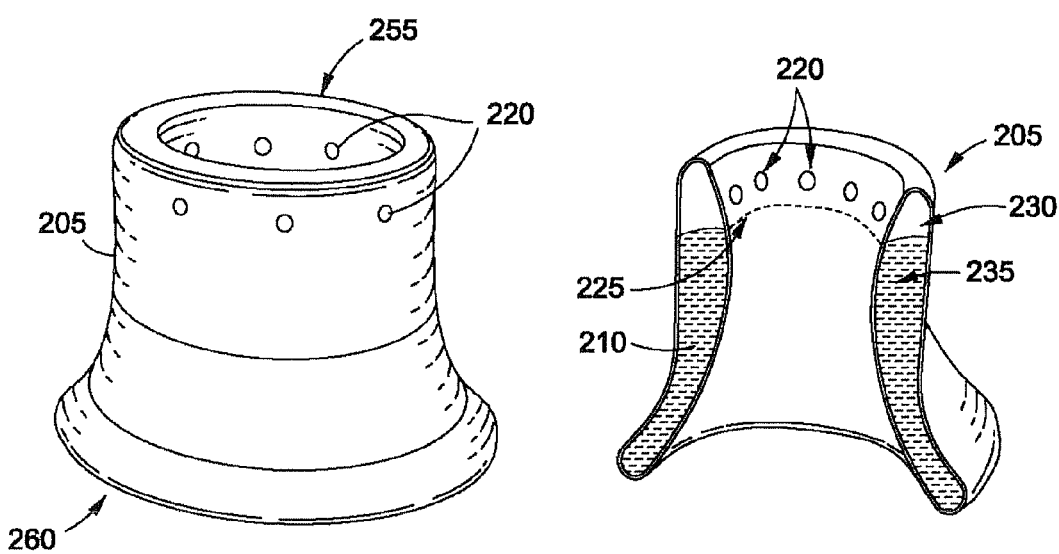
FIG. 2B illustrates the self-adjusting esophageal implant of FIG. 2A according to an embodiment of the present invention.
FIG. 2C illustrates a cross-sectional view of the self-adjusting esophageal implant of FIG. 2B according to an embodiment of the present invention.

FIG. 2B illustrates the esophageal implant device 205 outside of the patient's body and shown without the tissue anchors for the sake of clarity. The esophageal implant device 205 may be bell-shaped (or cylindrical-shaped with an outwardly tapered bottom end or hour-glass shaped) with the portion of the esophageal implant device 205 extending into the stomach of the patient flaring outwards (i.e., similar to an inverted funnel). That is, in one embodiment, the circumference of a bottom portion 260 of the esophageal implant device 205 where a food bolus exits is larger than a circumference of a top portion 255 where the food bolus enters the esophageal implant device 205.

As shown in the cross-sectional illustration of FIG. 2C, the esophageal implant device 205 may be compliant, low-durometer (e.g., 0-30 Shore A) and gel-filled or saline-filled. In one embodiment, the esophageal implant device 205 may be divided by a separating wall 225 into an anchoring portion 230 having the holes 220 and a compliant portion 235. The anchoring portion 230 may be unfilled or constructed out of a sturdier material such as a polymer, while the compliant portion 235 may be filled with a compliant gel or other appropriate filling 210. The filling 210 may be silicone or other gel materials (e.g., as derived from breast implant devices or dermal filling applications). The separating wall 225 prevents the filling 210 from entering into the anchoring portion 230.

In one or more alternative embodiments, the esophageal implant device 205 might not include a separating wall 225. Accordingly, the entire or substantially entire esophageal implant device 205 may be filled with the filling 210.

As shown above, for example in FIG. 2A, the esophageal implant device 205 may be fixed to the patient's esophageal lumen via a tissue fixation means 215.

Figure 2D:
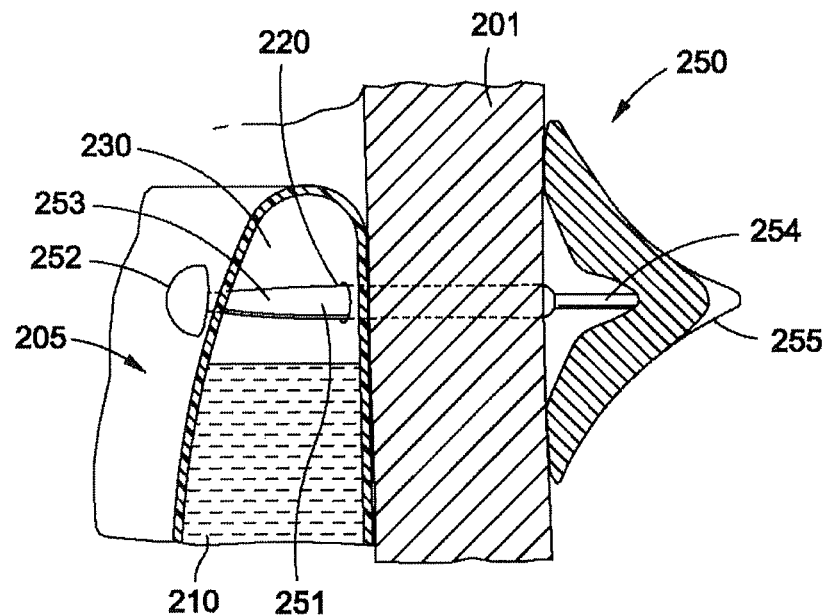
FIG. 2D illustrates an anchor member for the implant of FIG. 2A according to an embodiment of the present invention.

FIG. 2D illustrates one embodiment of a tissue fixation means, and in particular, a mesh tissue anchor 250. The mesh tissue anchor 250 may be fully collapsible to allow delivery via endoscopic instrumentation (e.g., a needle driver). After penetration through the mucosal-serosal tissue 201, the mesh tissue anchor 250 may expand to prevent immediate retraction back within the esophageal lumen.

More particularly, the mesh tissue anchor 250 may include a pin 251 and a collapsible pin anchor 255. The pin 251 may include a head portion 252 connected to a stem portion 253, which in turn is connected to an anchor interface 254 connected to the collapsible pin anchor 255. When collapsed, the collapsible pin anchor 255 may be configured to be smaller than the holes 220 such that the collapsible pin anchor 255 may be insertable into any one of the holes 220. The stem portion 253 may be substantially the same dimension or slightly smaller as any of the holes 220 to allow the stem portion 253 to engage and hold the pin 251 in place after the collapsible pin anchor 255 is inserted through any one of the holes 220. The head portion 252 may be configured to be larger than the holes 220 to prevent the pin 251 from slipping through the holes 220. After the collapsible pin anchor 255 pierces through the mucosal-serosal tissue 201, the collapsible pin anchor 255 may be expanded dimensionally to prevent the aforementioned retraction. In this manner, the mesh tissue anchor 250 fixes the esophageal implant device 205 to the patient's mucosal-serosal tissue 201.

Figure 2E:
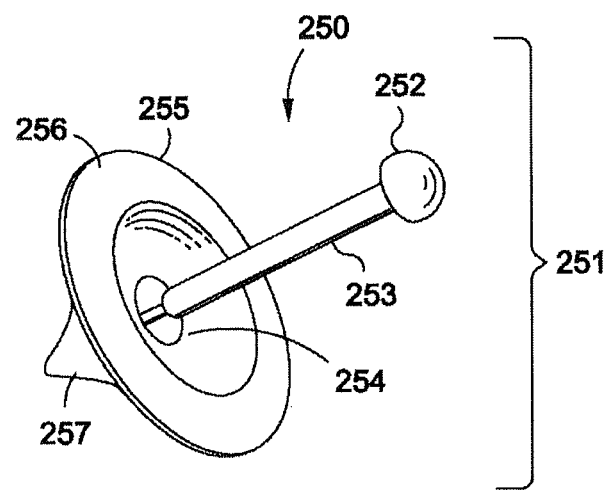
FIG. 2E illustrates the anchor member of FIG. 2D according to an embodiment of the present invention.

FIG. 2E illustrates the mesh tissue anchor 250 outside the patient's body for clarity. As shown here, the mesh tissue anchor 250 is in its expanded orientation. While not shown, the mesh tissue anchor 250 may also be collapsed in another orientation. In one embodiment, generally-speaking, the mesh tissue anchor 250 may be loosely analogous to the operation of an umbrella operable to be collapsed or expanded. The collapsible pin anchor 255 may include a supporting portion 256 designed to be smooth and flat and for contacting an outside surface of the patient's serosal tissue when the collapsible pin anchor 255 is expanded. The collapsible pin anchor 255 may further include an apex 257 for holding the pin 251 to the collapsible pin anchor 255.

In one embodiment, when expanded and positioned as shown in FIG. 2D, the collapsible pin anchor 255 may allow for tissue in-growth thereby providing even greater fixating potential and biocompatibility. In addition, discrete anchor implantation and/or removal may be performed by endoscopy.

Figure 2F:
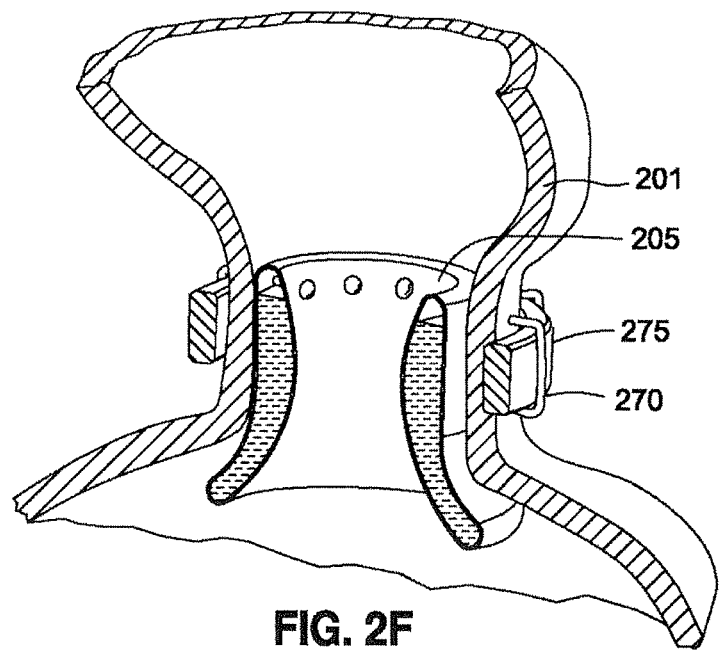
FIG. 2F illustrates a self-adjusting esophageal implant disposed within a patient's body according to an embodiment of the present invention.
Figure 2G:
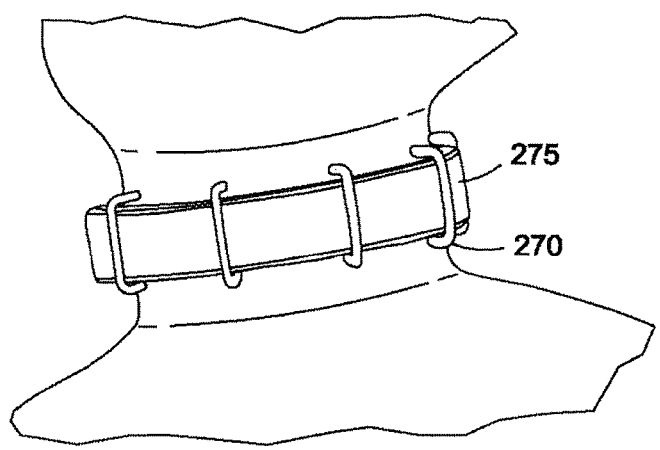
FIG. 2G illustrates an anchor member for the implant of FIG. 2F according to an embodiment of the present invention.
Figure 2H:
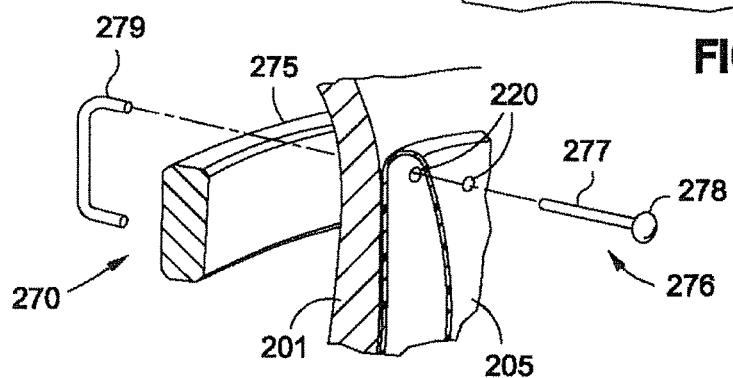
FIG. 2H illustrates the anchor member of FIG. 2F according to an embodiment of the present invention.

FIG. 2F-2H illustrates another example of a tissue fixation means. Here, tissue fixation may be accomplished using a combination of anchors that mate with a gastric band that wraps around the exterior of the patient's esophagus. The gastric band may be advantageous due to the proven longevity of the support (e.g., over 10 years) and further promoting satiety by providing a presence about the surrounding satiety nerves. Implantation and removal of this embodiment of fixation may be performed laparoscopically.

FIG. 2F illustrates one embodiment of how the esophageal implant device 205 may be attached to the patient's mucosal-serosal tissue 201 via anchors 270 and further holding the gastric band 275 in place.

More particularly, as shown in FIG. 2G, a plurality of anchors 270 may be positioned circumferentially and uniformly about the patient's esophagus. The anchors 270 advantageously hold the esophageal implant device 205 in place while also functioning similarly to belt loops creating a barrier against undesired movement in three directions with respect to the gastric band 275, thereby holding the gastric band 275 in place contacting the patient's esophagus.

FIG. 2H illustrates how the anchors 270 are placed into position. The anchors 270 may include a pin component 276 having a stem portion 277 and a head portion 278, and a hook component 279. The stem portion 277 of the pin component 276 may penetrate holes 220 of the esophageal implant device 205 and mucosal-serosal tissue 201 prior to being received and joined to the hook component 279. In this manner, the anchors 270 function to hold in place the esophageal implant device 205 on the mucosal side of the mucosal-serosal tissue 201 and the gastric band 275 on the serosal side the mucosal-serosal tissue 201.

FIGS. 3A-3E illustrates another embodiment of an esophageal implant device 300. The esophageal implant device 300 may be compliant, low-durometer (e.g., 0-30 Shore A), and low viscosity fluid filled. As shown, substantially the entire interior of the esophageal implant device 300 may be filled with a low viscosity fluid. For example, low viscosity fluids may include saline, silicone or other substances. Similar to the esophageal implant device 200 of FIG. 2A, the esophageal implant device 300 may emulate natural tissue behavior. However, the esophageal implant device 300 may further self-regulate internal pressures when implanted within the patient's esophagus 301. Furthermore, a "gating" effect may cause the bolus of food 350 traveling in the direction of arrow 310 to be further broken down as a result of the pressures on the esophagus 301.

Figure 3A:
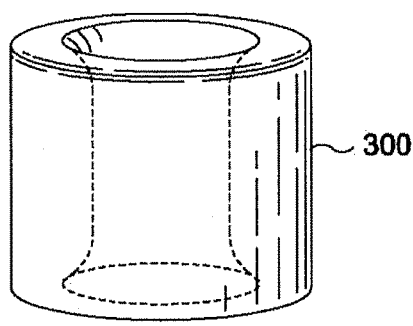
FIG. 3A illustrates one embodiment of a compliant, self-adjusting endoscopic device according to an embodiment of the present invention.
Figure 3B:
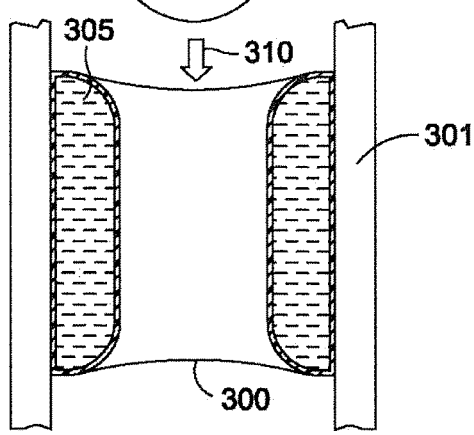
FIG. 3B illustrates the operation of the endoscopic device of FIG. 3A with respect to a bolus of food according to an embodiment of the present invention.

FIGS. 3B-3E illustrate how the esophageal implant device 300 may function. As shown in FIG. 3B, when the bolus of food 350 reaches the esophageal implant device 300 in the direction of arrows 310, the body 305 of the esophageal implant device 300 is in an equilibrium state.

Figure 3C:
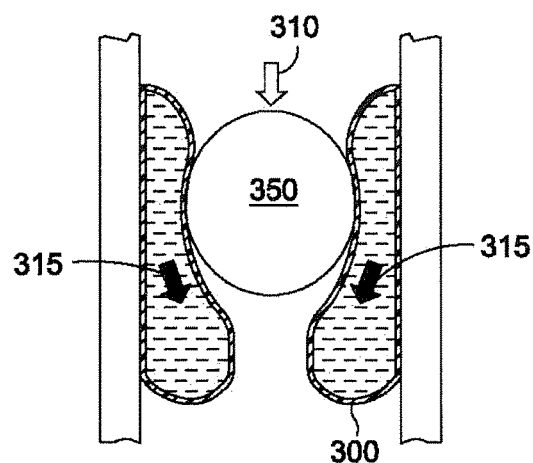
FIG. 3C illustrates the operation of the endoscopic device of FIG. 3A with respect to a bolus of food according to an embodiment of the present invention.
Figure 3D:
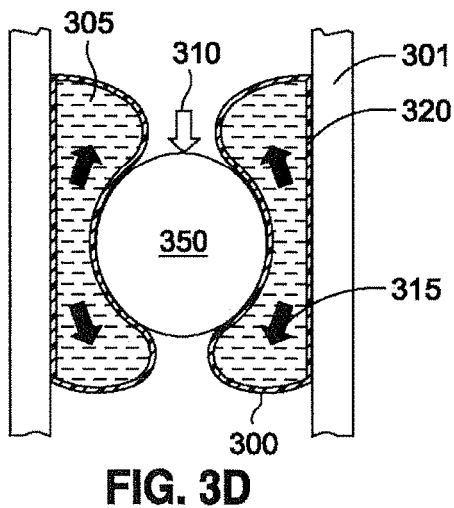
FIG. 3D illustrates the operation of the endoscopic device of FIG. 3A with respect to a bolus of food according to an embodiment of the present invention.
Figure 3E:
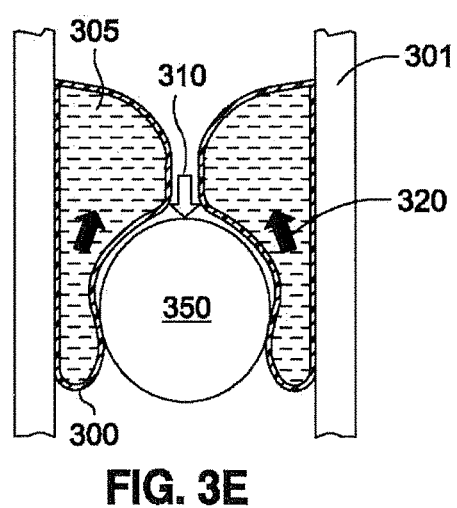
FIG. 3E illustrates the operation of the endoscopic device of FIG. 3A with respect to a bolus of food according to an embodiment of the present invention.

However, as the bolus of food 350 begins to transport through the esophageal implant device 300 as illustrated in FIG. 3C, the bolus of food 300 begins to exert a pressure causing the fluid within the esophageal implant device 300 to move in the direction of arrows 315. Here, the bolus 350 also applies an outward pressure and gates off the bottom portion of the esophageal implant device 300 (via the bulge beneath arrows 315) reservoir thereby slowing the digestion process and helping the patient feel satiated for a longer period of time.

As the bolus of food 350 continues to move downward in the direction of arrow 310, proximal to the middle portion of the esophageal implant device 300, the pressure exerted on the esophageal implant device 300 now causes some fluid to move in the direction of arrows 315 and some fluid to move in the direction of arrows 320, thereby facilitating the move of the bolus 350 downwards while also applying an outward pressure on the esophagus 301.

As peristalsis further transports the bolus of food 350 downward, proximal to the bottom portion of the esophageal implant device 300, the bolus of food 350 now exerts a pressure causing the fluid within the esophageal implant device 300 to move upwards in the direction of arrows 320.

As shown, the top portions of the esophageal implant device 300 above the arrows 320 bulges inward due to the influx of fluid thereby resulting in a gating effect. That is, the influx of fluid moving to the top portion of the esophageal implant device 300 above the arrows 320 momentarily prevents any other bolus from passing through the esophageal implant device 300.

Satiety may be correlated with bolus activity about the gastric band (e.g., moving up and back down), and therefore, in the manner illustrated in FIGS. 3B-3E, the patient may experience improved satiety after swallowing a bolus of food. In addition, the gating effect may assist to guide the bolus 350 through the esophageal implant device 300.

Other embodiments of an endoscopic device for the treatment of obesity may include a variable-sized opening for the passage of a bolus of food.

For example, a mechanical stoma may be provided. Due to the presence of mechanics, the relative ability for the mechanical stoma to emulate natural tissue motions may be less than the endoscopic devices 200 and 300 but still remain non-stiff.

FIGS. 4A-4D illustrate one embodiment of the mechanical stoma in the form of a conical valve 405. The conical valve 405 allows for regulating control over the overall restrictive capability of the esophageal implant 400. The restriction adjustment is based on the relative separation between the conical valve 405 and the housing 410. That is, the greater the separation, the less restriction the esophageal implant 400 can maintain. In one embodiment, the esophageal implant 400 may be physician adjusted.

As shown in FIG. 4A, the conical valve 405 is completely inserted into the housing 410, and as a result, the esophageal implant 400 is relatively very restrictive in this orientation.

Conversely, as shown in FIG. 4B, the conical valve 405 is not fully inserted into the housing 410, and as a result, the esophageal implant 400 is not as restrictive in this orientation as compared to the orientation of FIG. 4A. The arrow 420 illustrates a direction that the conical valve 405 may be manipulated to cause the esophageal implant 400 to be more restrictive. Conversely, manipulating the conical valve in the reverse direction may cause the esophageal implant 400 to be less restrictive.

FIGS. 4C and 4D illustrate a top view and a bottom view, respectively, of the esophageal implant 400 showing the gaps where the food may pass through between the conical valve 405 and the housing 410. As the conical valve 405 is manipulated to be increasingly restrictive, the gaps where the food may pass through become decreasingly smaller. In this manner, the conical valve 405 may be manipulated to control the level of restriction.

Manipulation of the conical valve 405 may be performed by the physician via a mechanical interface (e.g., a screw, spring or friction). Alternatively, the conical valve 405 may include a motor controllable by a remote computing device outside the body.

Figure 5A:
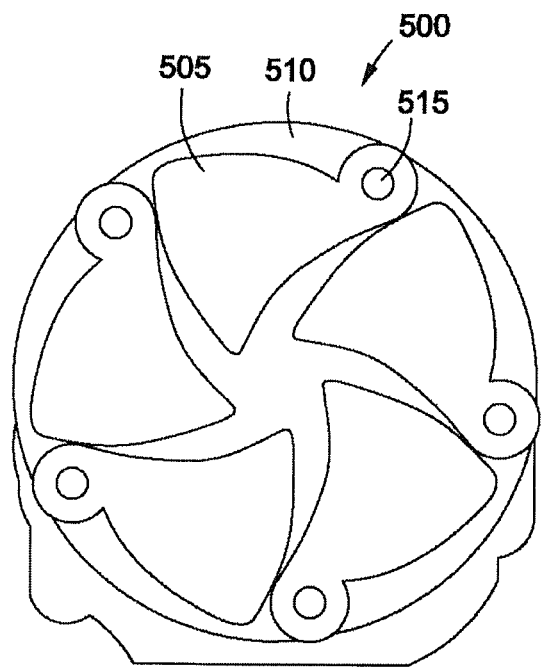
FIG. 5A illustrates an iris mechanism related to controlling the size of a stoma in a first position according to an embodiment of the present invention.
Figure 5B:
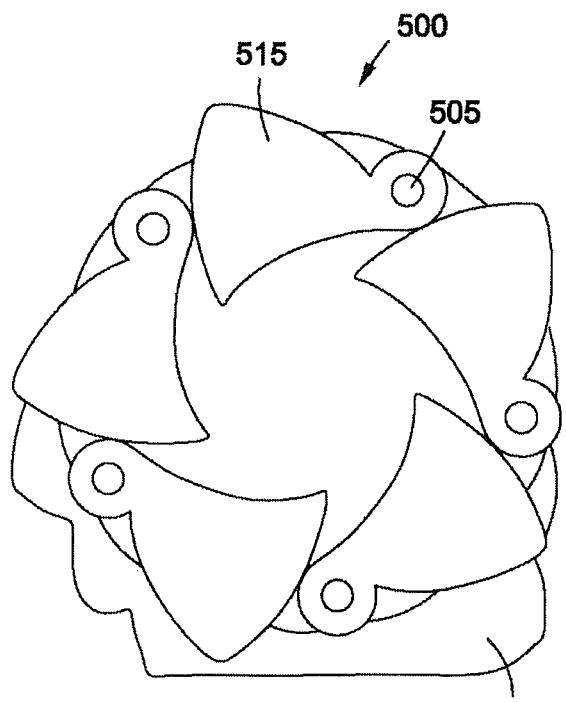
FIG. 5B illustrates the iris mechanism of FIG. 5A in a second position according to an embodiment of the present invention.

FIGS. 5A and 5B illustrate another embodiment of a mechanical stoma 500, here shown to include a plurality of plates 505 which pivot and/or overlap to vary the opening for the bolus of food.

FIG. 5A is a top view of the mechanical stoma 500 having a plurality of plates 505 attached to a body 510 via pivoting member 515. The plates 505 may be pivotably fixed to the body 510 to create a variably-sized opening for the passage of a bolus of food. As shown, the plates 505 are positioned in a relatively "closed" orientation resulting in a relatively small opening.

In one embodiment, the plates 505 may further engage one another such that movement of one plate may trigger the movement of an adjacent plate. Alternatively, the plates 505 might not contact each other and may be controlled independently. The physician may control the positioning of the plates 505 manually via an endoscopic device or the plates 505 may include a motor controllable by a remote computing device outside the body.

FIG. 5B illustrates a top view of the mechanical stoma 500 having the plurality of plates 500 positioned in a relatively "open" orientation resulting in a relatively large opening for the passage of food.

In another embodiment, an endoscopic device having a variably sized opening or iris may be provided to restrict a patient's consumption of food. For example, FIG. 6A illustrates a top view of an endoscopic device 600 defining an opening 605 for the passage of a bolus of food. In one embodiment, the endoscopic device 600 may be a biocompatible diaphragm 610 stretched across a frame 615, which may be rigid. The frame 615 may be attached to a patient's esophageal-gastric junction via tissue fixation means (e.g., as described herein). FIG. 6B illustrates a cross-sectional side view of the biocompatible diaphragm 610 fixed across the frame 615.

FIG. 6C illustrates the operation of the endoscopic device 600 with respect to a bolus of food 670. As the bolus of food 670 swallowed by the patient reaches the biocompatible diaphragm 610, the bolus of food 670 may cause a downward pressure on the opening 605 of the diaphragm 610 thereby temporarily enlarging the opening 605 and allowing the bolus of food 670 to pass through. FIG. 6D illustrates how the opening 605 of the endoscopic device 600 stretches to accommodate the bolus of food 670. The biocompatible diaphragm 610 as shown, defines one opening 605, but in other embodiments, may include additional openings of varying or uniform sizes.

The physician may be able to adjust the endoscopic device 600 in any of a plurality of ways to customize the size, shape and firmness of the diaphragm 600. For example, the physician may cut the opening 605 to size endoscopically or prior to implantation. The physician may also configure how taut the diaphragm 600 is when fixed to the frame 615 thereby controlling the size and/or shape of the opening 605, and further controlling the material's ability to stretch. In one or more embodiments, the material of the diaphragm (e.g., rubber) itself may be configured to be stiffer or more compliant as desired by the physician.

FIG. 7 illustrates a top view of an endoscopic device 700 having a "cross-hair shaped", variably sized opening 705 defined by a diaphragm 710, which may be stretched and/or fixed to a frame 715 according to an embodiment of the present invention. The endoscopic device 700 may operate and/or be configured similarly to endoscopic device 600 of FIG. 6A. Assuming all else equal, such a shaped opening may allow for better control of bolus transport through the device than the iris-shaped opening of FIG. 6A.

FIG. 8 illustrates a top view of an endoscopic device 800 having an ellipsoid-shaped, variably sized opening 805 defined by a diaphragm 810, which may be stretched and/or fixed to a frame 815 according to an embodiment of the present invention. The endoscopic device 800 may operate and/or be configured similarly to endoscopic device 600 of FIG. 6A. Assuming all else equal, the ellipsoid-shaped opening 805 may allow for easier passage of fluids due to being larger than the opening 605 of FIG. 6A. However, the configuration, and namely because the opening 805 is more narrow than the opening 605 of FIG. 6A, the passage of larger boluses of food may be more restricted with respect to the endoscopic device 800.

In certain embodiments, esophageal implants may include artificial esophageal stomas and stents or stent-like fixation means. Using such artificial stomas may provide substantial advantages including, but not limited to, (1) providing a noninvasive, non-surgical alternative to existing obesity treatment devices, (2) including stent or stent-like portions for positioning and fixating means to hold the artificial stoma in place, (3) providing non-invasive means for determining implant location within a patient's body due to being visible under fluoroscopy or other radiographic imagining, (4) having pliable and complaint characteristics making the artificial esophageal stoma obstruction tolerant, (5) allowing variability in the size of the stoma/stent (e.g., by removing a stoma/stent of one size and replacing it with a stoma/stent of a second size), and/or (6) allowing removal of the artificial esophageal stoma using non-surgical, full endoscopic instrumentation.

FIG. 9A illustrates one embodiment of an esophageal implant 900 positioned within a patient's esophagus 905. The esophageal implant 900 may include a stent portion 910 and an artificial stoma portion 915.

The esophageal implant 900 is shown outside the patient's body for clarity in FIG. 9B. The stent portion 910 may be constructed out of nitinol, nitinol-platinum alloys or other materials with similar properties and may be configured to have any of a number of different geometries to assist with fixation and migration resistance when implanted into the esophagus 905. The stent portion 910 may also include barbs, ribs, fins, struts or other outward members to further prevent migration and maintain fixation within the patient's esophagus 905. In addition, the stent portion 910 may be coupled with tissue fixation means (e.g., such as mesh anchor 250).

The stent portion 910 may be attached to the artificial stoma portion 915 via a lining portion 925. The lining portion 925 may be constructed out of silicone and may cover the stent portion 910 partially (as shown) or entirely (not shown). The lining portion 925 may be attached to the stent portion 910 and the artificial stoma portion 915 via any one of a number of different techniques including but not limited to (1) situating the lining portion 925 along the inner diameter of the stent portion 910 (e.g., in a "belt-and suspenders" type design), (2) overmolding the stoma shell over the stent and then filling the shell with gel, and/or (3) utilizing mechanical fixation means or other appropriate fixation means.

The artificial stoma portion 915 may be gel-filled and both pliable and compliant. For example, the artificial stoma portion 915 may operate in a manner similar to endoscopic devices 200 and 300 of FIGS. 2A and 3A, respectively.

The esophageal implant 900 may also include grasping members 920 fixed to the top of the stent portion 910 as shown in FIGS. 5B and 5C for easier implantation and/or removal. Alternatively and/or in addition, a suture running through the stent portion 910 may assist to collapse the esophageal implant 900 for removal.

In one or more embodiments, the esophageal implant 900 may act as a "funnel" such that the opening 935 at the top of the stent portion 910 may be larger than the opening 930 at the bottom of the artificial stoma portion 915 to guide a bolus of food and to provide the restrictive features of the artificial stoma portion 915.

Many variations to the esophageal implant 900 may be possible. For example, the artificial stoma portion 915 may be endoscopically removed leaving the stent portion 910 in place. In this manner, removal of the restrictive stoma portion 910 may be performed while enabling future reattachment of a similarly sized or differently sized stoma portion.

Other variations to the esophageal implant 900 may include changing the conical geometry to a cylindrical geometry over varied lengths, including flared ends or including ribs, fins or other barb-like features along the stent body to assist with fixation within the esophageal lumen and to prevent migration during normal and/or increased peristalsis. The stent portion 910 may also be braided or laser cut to improve the collapsibility of the esophageal implant 900 for delivery, opening force and compliance within the patient's body.

FIG. 9D is a close-up view of FIG. 9A showing the endoscopic device having the stent portion 910 located above the artificial stoma portion 915 (i.e., the artificial stoma portion 915 being distal to the stent portion 910).

However, alternative embodiments as shown in FIGS. 10 and 11 may include endoscopic devices 1000 and 1100 where the artificial stoma portion is located above the stent portion (as shown in FIG. 10 wherein the artificial stoma portion 1015 being proximal to the stent portion 1010) or contained within the stent portion (as shown in FIG. 11 wherein the stoma portion is integrated within the stent portion 1110 effectively reducing longitudinal contact on the mucosal tissue).

Certain embodiments have been disclosed to clarify the concepts including the above structural configurations. However, one skilled in the art will recognize that an endless number of implementations may be performed with the concepts herein. For example, the tube may be a catheter and may be used in other applications which require transferring fluid or gas.

Unless otherwise indicated, all numbers expressing quantities of ingredients, volumes of fluids, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, certain references have been made to patents and printed publications throughout this specification. Each of the above-cited references and printed publications are individually incorporated herein by reference in their entirety.

Specific embodiments disclosed herein may be further limited in the claims using consisting of or and consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

What is claimed is:

1. An endoscopic device insertable into a patient's digestive track and for the treatment of obesity, the endoscopic device comprising:
   a stent for migration resistance and for maintaining fixation to a patient's digestive tract when implanted into the patient's digestive tract, the stent defining a passageway for transporting a bolus of food, the stent defining an opening at a top of the stent;
   a pliable and compliant artificial stoma includes a compliance producing filling for emulating natural peristaltic behavior and further extending the passageway for transporting of the bolus of food, the artificial stoma coupled to the stent, the stoma defining an opening at the bottom of the stoma, wherein the opening at the top of the stent is larger than the opening at the bottom of the stoma; and a liner disposed between the stent and the artificial stoma, the liner configured to couple the stent to the artificial stoma and further extending the passageway for transporting the bolus of food.

2. The endoscopic device of claim 1, wherein the stent is constructed out of nitinol.

3. The endoscopic device of claim 1, wherein the stent further includes barbs for preventing migration and to maintain fixation to the patient's digestive tract.

4. The endoscopic device of claim 1, further comprising one or more grasping members fixed to a top of the stent, the grasping members for easier implantation or removal of the stent into the patient's digestive tract.

5. The endoscopic device of claim 1, wherein the opening defined by the stent and the opening defined by the artificial stoma are positioned at opposite ends of the passageway for transporting the bolus of food.

6. The endoscopic device of claim 1, wherein the endoscopic device is insertable into the patient's digestive track in one of a first configuration in which the stent is positioned closer to the patient's stomach than the artificial stoma and a second configuration in which the artificial stoma is positioned closer to the patient's stomach than the stent.

7. The endoscopic device of claim 1, wherein the stent portion is attached to the artificial stoma via the liner.

8. The endoscopic device of claim 1, wherein the liner is constructed out of silicone.

9. The endoscopic device of claim 1, wherein the liner covers the stent portion at least partially.

10. The endoscopic device of claim 1, wherein the stent is braided or laser cut.

11. The endoscopic device of claim 1, wherein the stent is frustoconical having a larger opening at the top of the stent and a smaller opening at a bottom of the stent.

12. The endoscopic device of claim 1, wherein an internal surface of the passageway is funnel-shaped.

13. The endoscopic device of claim 1, wherein an outer surface of the endoscopic device includes at least one of ribs, fins, and barbs to facilitate fixation of the endoscopic device within an esophageal lumen and to prevent migration during peristalsis.

14. The endoscopic device of claim 1, wherein the endoscopic device has an outer surface that includes conical and cylindrical portions over varied lengths of the endoscopic device.

15. The endoscopic device of claim 1, wherein an internal surface of the passageway includes conical and cylindrical portions over varied lengths of the endoscopic device.

16. The endoscopic device of claim 1, wherein the stent is disposed above the artificial stoma and the top of the stent defines a proximal end of the endoscopic device and the bottom of the artificial stoma defines a distal end of the endoscopic device.

17. The endoscopic device of claim 1, wherein the artificial stoma is integrated within the stent, such that the artificial stoma is disposed between the top of the stent and a bottom of the stent.

18. An endoscopic device insertable into a patient's digestive track and for the treatment of obesity, the endoscopic device comprising:
a stent for migration resistance and for maintaining fixation to a patient's digestive tract when implanted into the patient's digestive tract, the stent defining a passageway for transporting a bolus of food, the stent defining an opening at a top of the stent;
a pliable and compliant artificial stoma for emulating natural peristaltic behavior and further extending the passageway for transporting of the bolus of food, the artificial stoma coupled to the stent, the stoma defining an opening at the bottom of the stoma, wherein the opening at the top of the stent is larger than the opening at the bottom of the stoma; and
a liner disposed between the stent and the artificial stoma, the liner configured to couple the stent to the artificial stoma and further extending the passageway for transporting the bolus of food,
wherein when the stent is implanted in the esophagus, the opening at the bottom of the stoma is in fluid communication with the interior of the stomach, and wherein the stent, the stoma, and the liner are sized to be within the esophagus of the patient when the stent is implanted in the esophagus, wherein the artificial stoma is gel-filled and is pliable and compliant.

19. The endoscopic device of claim 18, wherein the artificial stoma includes a gel and a pliable and compliant tubular annular ring defining an annular space occupied by the gel, wherein the gel is sealed within the annular ring to prevent leakage of gel from the annular ring.

20. The endoscopic device of claim 19, wherein the gel and the annular ring are constructed to emulate natural peristaltic behavior to transport a bolus of food swallowed by the patient, wherein when a bolus of food contacts a top portion of the annular ring, the gel is transferred in a downward direction, and when the bolus of food contacts a middle portion of the annular ring, the fluid is transferred in both an upward and downward direction, and when the bolus of food contacts a bottom portion of the annular ring, the fluid is transferred in an upward direction.

* * * * *